(12) United States Patent
Nugent et al.

(10) Patent No.: US 7,015,320 B2
(45) Date of Patent: Mar. 21, 2006

(54) PROCESS FOR THE MANUFACTURE OF OPTICALLY ACTIVE 3-SUBSTITUTED LACTAMS BY ASYMMETRIC HYDROGENATION OF 3-ALKYLIDENELACTAMS

(75) Inventors: William A. Nugent, Wilmington, DE (US); Tai Yue, South Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 343 days.

(21) Appl. No.: 10/391,170

(22) Filed: Mar. 18, 2003

(65) Prior Publication Data

US 2004/0010139 A1 Jan. 15, 2004

Related U.S. Application Data

(60) Provisional application No. 60/365,612, filed on Mar. 19, 2002.

(51) Int. Cl.
| | | |
|---|---|---|
| C07D 205/08 | (2006.01) | |
| C07D 207/267 | (2006.01) | |
| C07D 207/26 | (2006.01) | |
| C07D 211/02 | (2006.01) | |
| C07D 223/10 | (2006.01) | |

(52) U.S. Cl. .................. 540/362; 540/524; 540/533; 546/290; 546/303; 546/301; 546/283.4; 548/517; 548/543; 548/551; 548/552

(58) Field of Classification Search .......... 548/517, 548/543, 551, 552; 546/290, 303, 301, 283.4; 540/362, 524, 533
See application file for complete search history.

(56) References Cited

U.S. PATENT DOCUMENTS 6,686,477 B1 * 2/2004 Boaz et al. .................. 548/551

FOREIGN PATENT DOCUMENTS

| WO | WO 9313095 | 7/1993 |
|---|---|---|
| WO | WO 0226705 | 4/2002 |

OTHER PUBLICATIONS

Ohta, J. Org. Chem 60, 357 (1995).*
Yue, T.-Y. et al., "Enantioselective Hydrogenation of 3-Alkylidenelactams: High-Throughput Screening Provides a Surprising Solution", J. Am. Chem. Soc., vol. 124, pp. 13692-13693 (2002).
Chan et al., "Iridium (III) hydride complexes for the catalytic anantioselective hydrogenation of imines", Univ. Louis Pasteur, J. Am. Chem. Soc. (1990), 112(25), 9400-1.
Margalef–Català, et al., "Heterogenised Iridium complexes for the asymmetric hydrogenation of imines", Universitat Rovira I Virgili, Tetrahedron: Asymmetry (2000), 11(7), 1469–1476.
Takeuchi, et al., "Asymmetric reactions. XIV. Asymmetric hydrogenation of N,N', –dimethyl–5–alkylidene– & (arylmethylene)hydantoins catalyzed by (achiral base)bis(dimethyl–glyoximato)cobalt(II)–chiral", Niigata Coll. Pharms. Bull. Chem. Soc. Jpn. (1987), 60(4), 1449–55.
Bakos et al., "Catalytic and structural studies of $Rh^1$ complexes of (–)–(2S,4S)–2,4–bis(diphenylphophino)pentane. Asymmetric hydrogenation of acetophenonebenzylimine and acetophenone", Journal of Organometallic Chemistry, 370(1989), pp. 263–276.
Macneil, et al., "Asymmetric Synthesis. Asymmetric Catalytic Hydrogenation Using Chiral Chelating Six–Membered Ring Diphosphones", J. Am. Chem. Soc., 1981, 103, pp. 2273–2280.
Hidemasa Takaya, "BINAP: An Efficient Chiral Element for Asymmetric Catalysis", Acc. Chem. Res. 1990, 23, pp. 345–350.
Mark J. Burk, "The DuPHOS Ligands—A Historical Account", Chemtracts—Organic Chemistry, 11, p. 787–802, 1998.

(Continued)

Primary Examiner—Mark L. Berch
(74) Attorney, Agent, or Firm—Mary VanAtten

(57) ABSTRACT

The present invention relates generally to processes for the efficient production optically active 3-substituted lactams of formula (I)

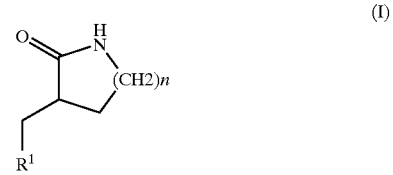

(I)

process, comprising:
contacting a compound of formula (II):

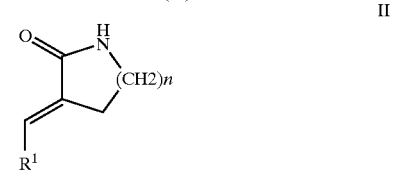

II with hydrogen under a suitable pressure in the presence of an iridium complex of the formula $(R^2)IrL^+X^-$ wherein L is a chelating diene, X is a non coordinating anion, and $R^2$ is selected from

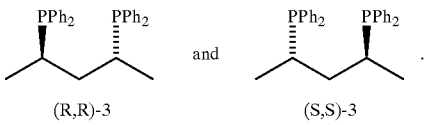

12 Claims, No Drawings

OTHER PUBLICATIONS

Inoguchi, et al., "Development of A New Six–Membered Chelating Chiral {Bisphosphine} rhodium Catalyst and Efficient Asymmetric Hydrogenation of (Z)–2–Acetamidocinnamic Acid[1]", *Synlett*, Jan. 1991, pp. 49–51.

Bose, et al., "Studies of Lactams—XXX1 Synthesis of Dihydropyrroles and Tetrahydropyridines as Intermediates for Bicyclic β–Lactams", *Tetrahedron*, vol. 30, pp. 3–9.

Zimmer, et al., "The Aldol Condensation of Aromatic Aldehydes with N–Acetyl–2–pyrrolidinone: Part II. Formation of Cinnamic Acids in the Synthesis of 3–Arylidene–2–pyrrolidinones", *Notes Department of Chemistry, University of Cincinnati*, vol. 3, Jun. 1966, pp. 232–234.

Zimmer, et al., "The Aldol Condensation of Aromatic Aldehydes with N–Acetyl–2–pyrrolidinone: Synthesis of 3–Arylidene–2–pyrrolidinones", *Notes Department of Chemistry, University of Cincinnati*, vol. 2, Jun. 1965, pp. 171–175.

Abstract of JP 2002255933 (Sep. 2002).

Abstract of JP 2000344754 (Dec. 2000).

Abstract of WO 02/040492 (May 2002).

Abstract of WO 02/012253 (Feb. 2002).

* cited by examiner

PROCESS FOR THE MANUFACTURE OF OPTICALLY ACTIVE 3-SUBSTITUTED LACTAMS BY ASYMMETRIC HYDROGENATION OF 3-ALKYLIDENELACTAMS

CROSS-REFERENCE TO RELATED APPLICATIONS

This application claims the priority benefit of U.S. Provisional Application No. 60/365,612, filed Mar. 19, 2002, the disclosure of which is incorporated herein by reference in its entirety.

FIELD OF INVENTION

The invention relates generally to processes for the preparation of enantiomerically enriched 3-substituted lactams as intermediates for the preparation of pharmaceutically active compounds.

BACKGROUND OF THE INVENTION

Modern organic chemists have as one goal the development of new synthetic routes for the controlled, efficient production of asymmetric compounds. Saturated carbon atoms, constituting the backbone of most organic compounds, are attached to adjacent carbon atoms through a tetrahedral arrangement of chemical bonds. If the four bonds are to different atoms or groups, the central carbon provides a chiral, or asymmetric, center and the compound therefore may have the ability to exist in two mirror image, or enantiomeric, forms. It is crucial when synthetic organic chemists attempt to prepare these asymmetric compounds to have a means to produce the desired enantiomer because compounds of the wrong enantiomeric form often lack desirable biological, physical or chemical properties.

A particularly attractive approach to the synthesis of optically active compounds is the catalytic asymmetric hydrogenation of unsaturated substrates. This approach is highly efficient because the only reagent is hydrogen gas, which is easily removed from the product after the reaction is complete. Such hydrogenations are carried out using a small amount of a metal complex typically bearing a chiral diphosphine ligand. In the vast majority of cases the metal atom in such catalysts is rhodium or ruthenium. Conventional wisdom dictates that the chelating diphosphine ligand should be highly rigid to effectively control the course of the hydrogenation. Two highly successful examples of rigid diphosphine ligands are BINAP [Noyori, R.; Takaya, H. *Acc. Chem. Res.* 1990, 23, 345] and the DuPHOS ligands [Burk, M. J. *Chemtracts Org. Chem.* 1998, 11, 787].

One class of unsaturated substrate where asymmetric hydrogenation has had limited success are the 3-alkylidenelactams. A single report describes the use of a ruthenium catalyst bearing a BINAP ligand to hydrogenate a series of 3-alkylidene-2-piperidones [Chung, J. Y. L. et. al. *Tetrahedron Lett.* 1995, 36, 739]. The selectivity of this process was limited for simple alkylidene derivatives but could be enhanced by introducing a functionalized alkylidene side-chain to provide an "internal ligand effect".

The use of 2,4-bis(diphenylphosphino)pentane (BDPP) ligands has been described but is not expected to impart enantioselectivity. This is because these ligands lack structural rigidity. It has been noted that, because of their flexibility, four conformers of a six-membered chelate ring containing metal-BDPP are possible, two of which are achiral chair conformations with the phenyl rings in an achiral array [MacNeil, P. A. et. al. *J. Am. Chem. Soc.* 1981, 103, 2273; Bakos, J. et. al. *J. Organometal. Chem.* 1989, 370, 263]. Thus the use of an iridium-BDPP catalyst to accomplish a challenging enantioselective hydrogenation of a C=C bond would not have been predicted by one skilled in the art. The particular iridium-BDPP catalyst utilized in the Applicants' process was previously studied as a potential catalyst for the hydrogenation of the C=N bond of imines; however, no enantioselectivity was observed unless the catalyst was adsorbed onto an insoluble clay support to provide additional rigidity [Margalef-Catala, R. et. al. *Tetrahedron Asymm.* 2000, 11, 1469].

Compounds disclosed in WO 00/35451 and similar publications are modulators of the CCR-3 receptor. Several of the compounds disclosed are prepared using 3-substituted-2-piperidones.

A need clearly exists for a process for the asymmetric hydrogenation of 3-alkylidenelactams which is practical, general, and highly enantioselective. The present invention provides such a process and affords 3-substituted lactams in a desired enantiomeric form. Other objects and advantages of the invention will become apparent to those skilled in the art upon reference to the detailed description, which hereinafter follows.

SUMMARY OF THE INVENTION

The present invention relates generally to processes for the efficient production of optically active 3-substituted lactams of formula (I)

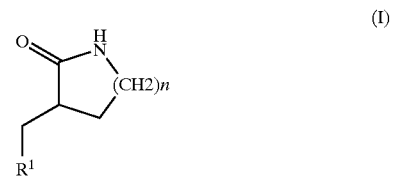

which has been achieved by the inventors' discovery that a compound of formula (I) or a pharmaceutically acceptable salt form thereof, is formed by a high yielding and chiral process, comprising:
contacting a compound of formula (II):

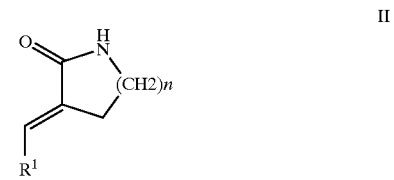

with hydrogen under a suitable pressure in the presence of an iridium complex of the formula $(R^2)IrL^+X^-$ wherein L is a chelating diene, X is a non coordinating anion, and $R^2$ is selected from

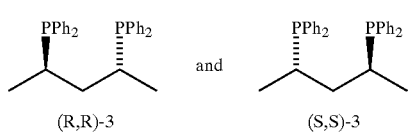

wherein $R^1$, $R^2$, L, X, and n are defined below.

DETAILED DESCRIPTION OF EMBODIMENTS OF THE INVENTION

[1] Thus, in a first embodiment, the present invention describes a novel process for the preparation of a compound of formula (I):

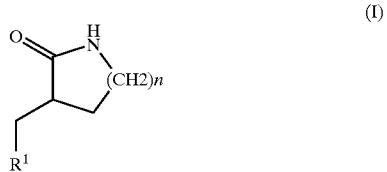

(I)

or a pharmaceutically acceptable salt form thereof wherein:
$R^1$ is selected from H, $C_{1-6}$ alkyl substituted with 0–3 $R^3$, $C_{3-6}$ cycloalkyl substituted with 0–3 $R^3$, and $C_{6-10}$ aryl substituted with 0–3 $R^3$, and a 5–6 membered heterocycle having 1–2 heteroatoms selected from O, N, and S, the heterocycle being substituted with 0–3 $R^3$;
$R^3$ is selected from $C_{1-4}$ alkyl, $C_{1-4}$ haloalkyl, F, Cl, Br, I, CN, $NO_2$, —S—$R^4$, —O—$R^4$, —$SO_2R^{4a}$, —C(O)$OR^{4a}$, —NHC(O)$R^4$, —C(O)NH$R^4$, —NHC(O)O$R^{4a}$, —OC(O)NH$R^{4a}$, —OC(O)$R^4$, and $C_{6-10}$ aryl substituted with 0–3 $R^5$;
$R^4$ is selected from H, $C_{1-4}$ alkyl, and phenyl;
$R^{4a}$ is selected from $C_{1-4}$ alkyl, and phenyl;
$R^5$ is selected from F, Cl, Br, I, CN, $NO_2$, —S—$R^4$, —O—$R^4$, —$SO_2R^4$, —C(O)$OR^{4a}$, —N($R^4$)$_2$, —NHC(O)$R^4$, —C(O)NH$R^4$, —OC(O)$R^4$, —C(O)O$R^4$, and phenyl;
n is selected from 0, 1, 2, 3;
the process comprising:
contacting a compound of formula (II)

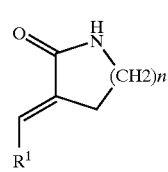

II with hydrogen under a suitable pressure in the presence of an iridium complex of the formula ($R^2$)Ir$L^+X^-$ wherein L is a chelating diene, X is a non coordinating anion, and $R^2$ is selected from

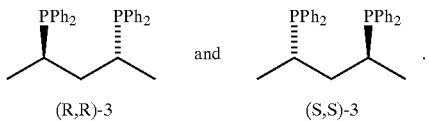

[2] In another embodiment, the present invention describes a novel process for the preparation of a compound of formula (I), wherein the compound of Formula 1 is optically active.

[3] In another embodiment, the present invention describes a novel process for the preparation of a compound of formula (I), wherein the compound of Formula 1 has an enantiomeric excess of greater than about 80%.

[4] In another embodiment, the present invention describes a novel process for the preparation of a compound of formula (I), wherein the compound of Formula 1 has a high level of enantiomeric purity.

[5] In another embodiment, the present invention describes a novel process for the preparation of a compound of formula (I), wherein $R^1$ is selected from H, $C_{1-6}$ alkyl substituted with 0–3 $R^3$, a $C_{6-10}$ aryl substituted with 0–3 $R^3$, wherein the aryl is selected from phenyl and naphthyl, and a a 5–6 membered heterocycle having 1–2 heteroatoms selected from O, N, and S, the heterocycle being substituted with 0–3 $R^3$, they heterocycle being selected from 2-furanyl, 3-furanyl, 2-thienyl, 3-thienyl, oxetanyl, tetrahydrofuranyl, or pyranyl;
$R^3$ is selected from $C_{14}$ alkyl, $CF_3$, F, Cl, Br, I, CN, $NO_2$, —O—$R^4$, —C(O)$OR^{4a}$, —NHC(O)$R^4$, —C(O)NH$R^4$, —OC(O)$R^4$, and phenyl substituted with 0–3 $R^5$.

[6] In another embodiment, the present invention describes a novel process for the preparation of a compound of formula (I), wherein
$R^1$ is selected from H, $C_{1-6}$ alkyl selected from methyl, ethyl, propyl, i-propyl, butyl, i-butyl, sec-butyl, t-butyl, and pentyl, phenyl substituted with 0–2 $R^3$, furanyl substituted with 0–1 $R^3$; and
$R^3$ is selected from $C_{14}$ alkyl, $CF_3$, F, Cl, Br, and I.

[7] In another embodiment, the present invention describes a novel process for the preparation of a compound of formula (I), wherein
L is selected from 1,5-cyclooctadiene and norbornadiene; and
X is selected from $BF_4^-$, $PF_6^-$, $SbF_6^-$, $ClO_4^-$, $AsF_6^-$, $O_3SCF_3^-$, $O_2CCF_3^-$, and $B(C_6F_6)_4^-$.

[8] In another embodiment, the present invention describes a novel process for the preparation of a compound of formula (I), wherein the catalyst is generated in the reaction mixture by sequential addition of an iridium complex of Formula $L_2Ir^+X^-$ and 1.0 to 1.1 molar equivalents of (R,R)-3 or (S,S)-3.

[9] In another embodiment, the present invention describes a novel process for the preparation of a compound of formula (I), wherein n is selected from 1 and 2.

[10] In another embodiment, the present invention describes a novel process for the preparation of a compound of formula (I), wherein $R^1$ is selected from the group consisting of phenyl, p-fluorophenyl, p-methoxyphenyl, p-trifluormethylphenyl, 2-furanyl, or n-propyl.

[11] In another embodiment, the present invention describes a novel process for the preparation of a compound of formula (I), wherein the process further comprises filtering the resultant solution through a bed of solid scavenger to remove catalyst residues.

[12] In another embodiment, the present invention describes a novel process for the preparation of a compound of formula (I), wherein the process further comprises removal of the reaction solvent by distillation, and crystallizing the product of Formula I to achieve a high level of enantiomeric purity.

In another embodiment, the present invention describes a novel process for the preparation of a compound of formula (I), wherein $R^1$ is selected from methyl, ethyl, propyl, i-propyl, butyl, phenyl substituted with 0–1 $R^3$.

In another embodiment, the present invention describes a novel process for the preparation of a compound of formula (I), wherein $R^3$ is selected from F, Cl, Br, $CF_3$, and —$OCH_3$.

DEFINITIONS

The following terms and abbreviations are used herein and defined as follows. The abbreviation: "THF" as used herein means tetrahydrofuran, "HPLC" as used herein means high performance liquid chromatograpy, "GC" as used herein means gas chromatography, "PCT" as used herein means process control test, and "e.e." as used herein means enantiomeric excess.

The reactions of the synthetic methods claimed herein are carried out in suitable solvents which may be readily selected by one skilled in the art of organic synthesis, the suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction, suitable solvents for a particular reaction or work-up following the reaction may be selected. Such suitable solvents, as used herein may include, by way of example and without limitation, chlorinated solvents, hydrocarbon solvents, ether solvents, polar protic solvents and polar aprotic solvents.

Suitable ether solvents include, but are not limited to dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, and t-butyl methyl ether.

The compounds described herein may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. Methods on how to prepare optically active forms from optically active starting materials are known in the art, such as by resolution of racemic forms or by synthesis. All chiral, diastereomeric, racemic forms and all geometric isomeric forms of a structure are intended.

The term "chiral" means "existing as a pair of enantiomers". These stereoisomers, designated the R and S enantiomers are mirror images of one another. A chiral material may either contain an equal amount of the R and S isomers (in which case it is called "racemic") or it may contain inequivalent amounts of R and S isomer (in which case it is called "optically active"). The extent of this inequivalence is measured as the "enantiomeric excess".

The term "enantiomeric excess" means the difference between the percent of R enantiomer and the percent of S enantiomer of an optically active compound. For example, a compound that contains 75% S isomer and 25% R isomer will have an enantiomeric excess of 50%.

The term "high level of enantiomeric purity" means having an enantiomeric excess of greater or equal to about 90%.

The term "enantioselective" means having the ability to produce a product in optically active form.

As used herein, the abbreviation "BDPP" is intended to mean (R,R)-2,4-bis(diphenylphosphino)pentane or (S,S)-2,4-bis(diphenylphosphino)pentane which have the structures (R,R)-3 and (S,S)-3 respectively. This chelating diphosphine ligand is also known in the art as "skewphos".

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. $C_{1-8}$ alkyl, is intended to include $C_1$, $C_2$, $C_3$, $C_4$, $C_5$, $C_6$, $C_7$, and $C_8$ alkyl groups. "Haloalkyl" is intended to include both branched and straight-chain saturated aliphatic hydrocarbon groups having the specified number of carbon atoms, substituted with 1 or more halogen (for example —$C_vF_w$, where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl.

As used herein "halo" or "halogen" refers to fluoro, chloro, bromo and iodo.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. In another aspect of the invention, the heterocycles include, but are not limited to, 2-furanyl, 3-furanyl, 2-thienyl, 3-thienyl, oxetanyl, tetrahydrofuranyl, or pyranyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1, 2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

As used herein, "stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

As used herein, "suitable pressure" is intended to indicate a pressure sufficient to achieve a complete reaction after about 72 hours or less. Suitable pressures range from atmospheric to any pressure obtainable in a laboratory or industrial plant. For practical operations, a pressure of between 1 and 100 atmospheres of hydrogen is used. A pressure of between 1 and 20 atmospheres of hydrogen may be utilized Alternatively, a pressure of 3 to 10 atmospheres may be utilized. Furthermore, a pressure of 3, 4, 5, 6, 7, 8, 9, or 10 atmospheres may be utilized.

As used herein, "chelating diene" is intended to indicated a diene in which both double bonds of the diene structure can simultaneously bind to the iridium atom in (DBPP)$IrL^+X^-$.

As used herein, "non-coordinating anion" is intended to indicate a negatively charged ion which is sufficiently non-nucleophilic that the catalyst dissociates to afford the cationic species (DBPP)$IrL^+$. A suitable anion should be the conjugate base of an acid whose dissociation constant is equal to or greater than about 1.8.

As used herein, "substituted" is intended to indicate that one or more hydrogens on the atom or ring indicated in the expression using "substituted" is replaced with a selection from the indicated group(s), provided that the indicated atom's normal valency is not exceeded, and that the substitution results in a stable compound.

The present invention includes all isotopes of atoms occurring in the intermediates or final compounds. Isotopes include those atoms having the same atomic number but different mass numbers. By way of general example and without limitation, isotopes of hydrogen include tritium and deuterium; isotopes of carbon include $^{13}C$ and $^{14}C$.

Combination of substituents and/or variables are permissible only if such combinations result in stable compounds. By stable compound or stable structure it is meant herein a compound that is sufficiently robust to survive isolation to a useful degree of purity from a reaction mixture.

When any variable (for example but not limited to $R^1$ and $R^3$) occurs more than one time in any constituent or in any formula, its definition on each occurrence is independent of its definition at every other occurrence. Thus, for example, if a group is shown to be substituted with 0–3 $R^3$, then said group may optionally be substituted with up to 3 $R^3$ and $R^3$ at each occurrence is selected independently from the defined list of possible $R^3$.

As used herein, "pharmaceutically acceptable salt" refer to derivatives of the disclosed compounds wherein the intermediates or final compound are modified by making acid or base salts of the intermediates or final compounds. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the intermediates or final compounds include the conventional non-toxic salts or the quaternary ammonium salts from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts are generally prepared by reacting the free base or acid with stoichiometric amounts or with an excess of the desired salt-forming inorganic or organic acid or base in a suitable solvent or various combinations of solvents.

The pharmaceutically acceptable salts of the acids of the intermediates or final compounds are prepared by combination with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

A preferred form of the invention provides a method for preparation of 3-substituted lactams of Formula I having a high level of enantiomeric purity via hydrogenation of a 3-alkylidenelactam of Formula II. The general scheme can be pictured as follows:

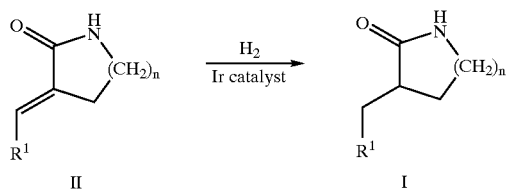

II        I

The reaction comprises: a) contacting a solution of substrate of Formula II with hydrogen in the presence of a soluble iridium catalyst bearing a BDPP ligand of Formula 3, b) optionally filtering the resultant solution through a bed of solid scavenger to remove catalyst residues, c) removal of the reaction solvent by distillation, and d) optionally crystallizing the product of Formula I to achieve a high level of enantiomeric purity.

The Applicants have discovered that asymmetric hydrogenation of II to provide optically active I can be accomplished using a soluble iridium catalyst of formula (BDPP) IrL$^+$X$^-$ where L is a chelating diene and X is a non-coordinating anion. Suitable L includes 1,5-cyclooctadiene or norbornadiene. Suitable X includes, but is not limited to, ClO$_4$$^-$, BF$_4$$^-$, PF$_6$$^-$, SbF$_6$$^-$, AsF$_6$$^-$, O$_3$SCF$_3$$^-$, O$_2$CCF$_3$$^-$, or B(C$_6$F$_6$)$_4$$^-$. The BDPP ligand has structure (R,R)-3 or (S,S)-3:

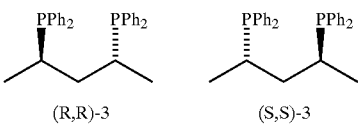

(R,R)-3        (S,S)-3 where the choice of which ligand enantiomer is used depends on the desired conformation of product I. For example, hydrogenation of 3-(p-fluorobenzylidene)-2-piperidone using (S,S)-3 affords predominantly the (S)-enantiomer of 3-(p-fluorobenzyl)-2-piperidone.

The soluble iridium catalyst may be prepared in a separate operation via treatment of the corresponding iridium salt of formula L$_2$IrX with 1.0 to 1.1 molar equivalents of (R,R)-3 or (S,S)-3 in a polar aprotic solvent, examples of which include, but are not limited to, dichloromethane, chloroform, chlorobenzene, and chlorobutane. Addition of an appropriate anti-solvent then precipitates the catalyst which is collected by filtration. Suitable anti-solvents include, but are not limited to, diethyl ether, dibutyl ether, and methyl t-butyl ether or other ether solvents. Alternatively, the soluble iridium catalyst may be generated in the reaction mixture by sequential addition of the corresponding iridium salt of formula L$_2$IrX followed by 1.0 to 1.1 molar equivalents of (R,R)-3 or (S,S)-3.

Any procedure known in the art can be used to prepare the 3-alkylidenelactam of Formula II that is used as the starting material. One such procedure involves deprotonating a lactam which has been protected as its N-acetamide derivative, using butyllithium at low temperature. Trapping of the resultant carbanion with an appropriate aldehyde affords the compound of Formula II [Bose, A. K. et. al. *Tetrahedron*, 1974, 30, 3; Zimmer, H. et. al. *J. Heterocyclic Chem.* 1965, 2, 171].

The hydrogenation pressure can be from 1 to 100 atmospheres (0.1 to 10 MPa). Alternatively, a pressure of 10 to 50 atmospheres (0.1 to 10 Mpa). For convenience, a pressure of 1 to 10 atmospheres (0.1 to 1.0 MPa) can be used.

The hydrogenation is carried out in a neutral protic or aprotic solvent. Suitable solvents include but are not limited to dichloromethane, ethyl acetate, tetrahydrofuran, methanol, ethanol, and isopropanol or mixtures thereof.

The reaction is carried out between 0° C. and 100° C. Hydrogenation rates are fastest at the upper end of this temperature range while enantioselectivity is highest at the lower end of the range. To balance these factors, hydrogenation is alternatively carried out between 20° C. and 50° C., or alternatively, between 20° C. and 40° C.

For practical operation, the molar ratio of substrate to catalyst should be from about 50:1 to about 1000:1, or alternatively between 50:1 and 500:1, or between 200:1 and 500:1.

In some cases it is useful to remove the catalyst residues from the product solution by filtering through a bed of a solid scavenger. Suitable scavengers for this purpose include silica, alumina, montmorollinite clay, or activated carbon.

The products of the invention can easily be converted into chiral intermediates useful in the manufacture of pharmaceuticals. Optically active 3-substituted lactams I can be converted to the corresponding 3-substituted cyclic amines without loss of activity by methods well known in the art. Moreover the nitrogen atom in either lactams I or the corresponding amines undergo C—N bond formation with alkylating agents such as alkyl halides or alkyl sulfonates which further increases their utility as pharmaceutical intermediates.

Although the Applicants contemplate many possible uses for the instant invention, possible examples include intermediates for orally active fibrinogen receptor antagonists as well as CCR3 inhibitors useful as anti-inflammatory drugs.

EXAMPLES

The 3-alkylidenelactam starting materials II were prepared by standard literature procedures [Bose, A. K. et. al. *Tetrahedron*, 1974, 30, 3; Zimmer, H. et. al. *J. Heterocyclic Chem.* 1965, 2, 171] from the corresponding unsubstituted lactams and aldehydes. The lactam and aldehyde starting materials were purchased from Aldrich Chemical Co., Milwaukee, Wis. The BDPP ligands (R,R)-3 and (S,S)-3 were purchased from Strem Chemical Company, Newburyport, Mass. and were used as received or from Digital Specialty Chemicals, Ltd., Mississauga, Ontario, Canada in which case the ligands were recrystallized from isopropanol prior to use. Bis(cyclooctadiene)iridium(T) tetrafluoroborate was purchased from Strem Chemical Company, Newburyport, Mass. or from Colonial Metals, Inc., Elkton, Md. and was used as received. Chiral HPLC analytical methods were developed using racemic samples of I prepared by hydrogenation of the corresponding substrates II over a 5% palladium on carbon catalyst. The Chiralpak AD, Chiralpak AS, and Chiralpak OD columns used to determine enantiomeric purity of products I were purchased from Chiral Technologies, Inc., Exton, Pa. NMR spectra were obtained at 25° C. in $CDCl_3$ and field strengths for the various nuclei were as follows: $^1H$ (400.1 MHz), $^{13}C$ (100.6 MHz), $^{19}F$ (376.5 MHz), $^{31}P$ (162.0 MHz).

The following non-limiting examples are intended to further illustrate the invention.

Example 1

The soluble iridium catalyst was prepared as follows. In a nitrogen-filled glove box, (S,S)-2,4-bis(diphenylphosphino)pentane (4.40 g, 100 mmol) and bis(1,5-cyclooctadiene)iridium(I) tetrafluoroborate (4.9 g, ca. 91% purity, 91 mmol) were dissolved in dichloromethane (50 mL). Diethyl ether (100 mL) was added dropwise to the stirred solution. The resultant precipitate was collected by filtration to afford [(S,S)-BDPP]Ir(COD)$BF_4$ (7.43 g,) as a red-violet microcrystalline solid. The $^{31}P$ NMR spectrum was a singlet at δ 16.7 ppm and was free of unreacted BDPP as indicated by the absence of a resonance at δ 0.5 ppm.

Example 2

This example describes the preparation of 1 where n=2 and $R^1$=p-fluorophenyl. In a nitrogen-filled glove box, a Fisher-Porter tube was charged with iridium catalyst prepared as in Example 1 (20 mg, 0.024 mmol) and 3-(p-fluorobenzylidene)-2-piperidone (1.00 g, 4.9 mmol). Tetrahydrofuran (5 mL) and dichloromethane (5 mL) were added and the system was flushed 4 times with hydrogen and pressured to 60 psi (0.5 MPa) $H_2$. After 18 h the reaction mixture was filtered through a short pad of silica. The solvent was removed at reduced pressure to afford (S)-3-p-flurorobenzyl-2-piperidone (I, $R^1$=p-fluorophenyl, n=2, 0.97 g, 97%) as a white crystalline solid. Chiral HPLC analysis (Chiralpak AS, 60% heptane, 39.2% isopropanol, 0.4% trifluoroacetic acid, 0.4% n hexylamine, 40° C.) indicated that conversion was 100% and the enantiomeric excess was 90%. $^{19}F$ NMR: δ –117.63; $^{13}C$ NMR δ 20.18, 24.33, 35.56, 41.27, 41.76, 114.06 (d, J=21 Hz), 129.61, 134.44, 160.42 (d, J=241 Hz), 173.49; $^1H$ NMR: δ 1.43 (m, 1H), 1.57–1.89 (m, 3H), 2.50 (m, 1H), 2.71 (app. dd, 1H), 3.29 (m, 3H), 6.01 (br s, 1H), 6.98 (m, 2H), 7.16 (m, 2H).

Example 3

This example describes the preparation of I where n=1 and $R^1$=p-fluorophenyl. In a nitrogen-filled glove box, a Fisher-Porter tube was charged with iridium catalyst prepared as in Example 1 (10 mg, 0.012 mmol) and 3-(p-fluorobenzylidene)-2-pyrrolidinone (250 mg, 1.3 mmol). Methanol (3 mL) and dichloromethane (3 mL) were added and the system was flushed 4 times with hydrogen and pressured to 60 psi (0.5 MPa) $H_2$. After 18 h the reaction mixture was filtered through a short pad of silica. The solvent was removed at reduced pressure to afford 3-p-fluorobenzyl-2-pyrrolidinone (250 mg, 100%) as a white crystalline solid. Chiral HPLC analysis (Chiralpak OD, 95% heptane, 4.9% isopropanol, 0.05% trifluoroacetic acid, 0.05% n-hexylamine, 40° C.) indicated that conversion was 100% and the enantiomeric excess was 88%. $^{19}F$ NMR δ –117.39; $^{13}C$ NMR δ 26.92, 35.90, 40.44, 42.88, 115.44 (d, J=21 Hz), 130.58, 135.21, 161.77 (d, J=241 Hz), 179.72; $^1H$ NMR: δ 1.83 (m, 1H), 2.15 (m, 1H), 2.66 (m, 2H), 3.11–3.32 (m. 3H), 6.47 (br s, 1H), 7.00 (m, 2H), 7.15 (m, 2H).

Example 4

This example describes the preparation of I where n=3 and $R^1$=p-fluorophenyl. In a nitrogen-filled glove box, a Fisher-Porter tube was charged with iridium catalyst prepared as in Example 1 (10 mg, 0.012 mmol) and 3-(p-fluorobenzylidene)caprolactam (250 mg, 1.1 mmol). Methanol (3 mL) and dichloromethane (3 mL) were added and the system was flushed 4 times with hydrogen and pressured to 60 psi (0.5 MPa) $H_2$. After 18 h the reaction mixture was filtered through a short pad of silica. The solvent was removed at reduced pressure to afford 3-(p-fluorobenzyl) caprolactam (230 mg, 92%) as a white crystalline solid. Chiral HPLC analysis (Chiralpak AS, 60% heptane, 39.2% isopropanol, 0.4% trifluoroacetic acid, 0.4% n-hexylamine, 40° C.) indicated that conversion was 100% and the enantiomeric excess was 67%. $^{19}F$ NMR δ –117.99; $^{13}C$ NMR δ 28.93, 29.47, 29.94, 36.73, 42.28, 45.65, 115.18 (d, J=21 Hz), 130.81, 136.47, 161.49 (d, J=241 Hz), 179.79; $^1H$ NMR: δ 1.43 (m, 3H), 1.70 (m, 1H), 1.76 (m, 1H), 1.91 (m, 1H), 2.54 (app. dd, 1H), 2.67 (m, 1H), 3.12–3.31 (m, 3H), 6.78 (br s, 1H), 6.96 (m, 2H), 7.14 (m, 2H).

Example 5

This example describes the preparation of I where n=2 and $R^1$=phenyl. In a nitrogen-filled glove box, a Fisher-Porter tube was charged with iridium catalyst prepared as in Example 1 (10 mg, 0.012 mmol) and 3-(benzylidene)-2-piperidone (250 mg, 1.3 mmol). Methanol (3 mL) and dichloromethane (3 mL) were added and the system was flushed 4 times with hydrogen and pressured to 60 psi (0.5 MPa) $H_2$. After 18 h the reaction mixture was filtered through a short pad of silica. The solvent was removed at reduced pressure to afford 3-benzyl-2-piperidone (240 mg, 96%) as a white crystalline solid. Chiral HPLC analysis (Chiralpak AS, 60% heptane, 39.2% isopropanol, 0.4% trifluoroacetic acid, 0.4% n-hexylamine, 40° C.) indicated that conversion was 100% and the enantiomeric excess was 83%. $^{13}C$ NMR: δ 20.10, 24.33, 36.42, 41.31, 41.74, 125.11, 127.32, 128.21, 138.84, 173.69;

$^1H$ NMR: δ 1.45 (m, 1H), 1.57–1.87 (m, 3H), 2.52 (m, 1H), 2.64 (m, 1H), 3.28 (m, 2H), 3.40 (app. dd, 1H), 6.55 (br s, 1H), 7.12–7.40 (m, 5H).

Example 6

This example describes the preparation of I where n=2 and $R^1$=p-methoxyphenyl. In a nitrogen-filled glove box, a Fisher-Porter tube was charged with iridium catalyst prepared as in Example 1 (10 mg, 0.012 mmol) and 3-(p-methoxybenzylidene)-2-piperidone (250 mg, 1.2 mmol). Methanol (3 mL) and dichloromethane (3 mL) were added and the system was flushed 4 times with hydrogen and pressured to 60 psi (0.5 MPa) $H_2$. After 18 h the reaction mixture was filtered through a short pad of silica. The solvent was removed at reduced pressure to afford 3-p-methoxybenzyl-2-piperidone (230 mg, 92%) as a white crystalline solid. Chiral HPLC analysis (Chiralpak AS, 60% heptane, 39.2% isopropanol, 0.4% trifluoroacetic acid, 0.4% n-hexylamine, 40° C.) indicated that conversion was 100% and the enantiomeric excess was 83%. $^{13}$C NMR: δ 21.32, 25.49, 36.72, 42.56, 43.11, 55.40, 113.93, 130.37, 131.99, 158.18, 174.93; $^1$H NMR: δ 1.44 (m, 1H), 1.62 (m, 1H), 1.68–1.75 (m, 2H), 2.50 (m, 1H), 2.64 (app. dd, 1H), 3.20–3.37 (m, 3H), 3.79 (s, 3H), 6.82 (d, J=9 Hz, 2H), 7.09 (br s, 1H), 7.12 (d, J=9 Hz, 2H).

Example 7

This example describes the preparation of I where n=2 and R$^1$=p-trifluoromethylphenyl. In a nitrogen-filled glove box, a Fisher-Porter tube was charged with iridium catalyst prepared as in Example 1 (10 mg, 0.012 mmol) and 3-(p-fluorobenzylidene)-2-piperidone (250 mg, 1.0 mmol). Methanol (3 mL) and dichloromethane (3 mL) were added and the system was flushed 4 times with hydrogen and pressured to 60 psi (0.5 MPa) H$_2$. After 18 h the reaction mixture was filtered through a short pad of silica. The solvent was removed at reduced pressure to afford 3-p-trifluoromethylbenzyl-2-piperidone (240 mg, 96%) as a white crystalline solid. Chiral HPLC analysis (Chiralpak AS, 60% heptane, 39.2% isopropanol, 0.4% trifluoroacetic acid, 0.4% n-hexylamine, 40° C.) indicated that conversion was 100% and the enantiomeric excess was 87%. $^{19}$F NMR: δ −62.78; $^{13}$C NMR δ 21.50, 25.70, 37.40, 42.50, 42.79, 124.26 (q, J=224 Hz), 125.46, 128.67 (q, J=32 Hz), 144.32, 174.25; $^1$H NMR: δ 1.42 (m, 1H), 1.60–1.89 (m, 3H), 2.58 (m, 1H), 2.79 (app. dd, 1H), 3.31 (m, 2H), 3.43 (app. dd, 1H), 7.10 (br s, 1H), 7.34 (d, J=8 Hz, 2H), 7.53 (d, J=8 Hz, 2H).

Example 8

This example describes the preparation of I where n=2 and R$^1$=2-furanyl. In a nitrogen-filled glove box, a Fisher-Porter tube was charged with iridium catalyst prepared as in Example 1 (10 mg, 0.012 mmol) and 3-(2-furanylmethylidene)-2-piperidone (250 mg, 1.4 mmol). Methanol (3 mL) and dichloromethane (3 mL) were added and the system was flushed 4 times with hydrogen and pressured to 60 psi (0.5 MPa) H$_2$. After 18 h the reaction mixture was filtered through a short pad of silica. The solvent was removed at reduced pressure to afford 3-(2-furanylmethyl)-2-piperidone (230 mg, 92%) as a white crystalline solid. Chiral HPLC analysis (Chiralpak AD, 85% heptane, 15% ethanol, 30° C.) indicated that conversion was 100% and the enantiomeric excess was 95%. $^{13}$C NMR: δ 21.55, 26.12, 29.99, 40.91, 42.57, 106.80, 110.39, 141.38, 153.99, 174.20; $^1$H NMR: δ 1.49 (m, 1H), 1.68 (m, 1H), 1.75–1.91 (m, 2H), 2.62 (m, 1H), 2.82 (m, 1H), 3.29 (m, 3H), 6.06 (m, 1H), 6.29 (m, 1H), 7.29 (m, 1H), 7.34 (br s, 1H).

Example 9

This example describes the preparation of I where n=2 and R$^1$=n-propyl. In a nitrogen-filled glove box, a Fisher-Porter tube was charged with iridium catalyst prepared as in Example 1 (8 mg, 0.010 mmol) and 3-(butylidene)-2-piperidone (150 mg, 1.0 mmol). Methanol (2 mL) and dichloromethane (2 mL) were added and the system was flushed 4 times with hydrogen and pressured to 60 psi (0.5 Mpa) H$_2$. After 18 h the reaction mixture was filtered through a short pad of silica. The solvent was removed at reduced pressure to afford 3-butyl-2-piperidone (140 mg, 93%) as a white crystalline solid. Chiral gas chromatographic analysis (Rt-GammaDex SA column, 130° C. for 5 min, then programmed to 200° C. at 10°/min) indicated that conversion was 95% and the enantiomeric excess was 90%. $^{13}$C NMR: δ 14.24, 21.27, 22.85, 26.04, 29.25, 31.36, 40.96, 42.38, 176.02; $^1$H NMR: δ 0.91 (t, J=7, 3H), 1.22–1.58 (m, 6H), 1.70 (m, 1H), 1.79–2.00 (m, 3H), 2.24 (m, 1H), 3.29 (m, 2H), 7.25 (br s, 1H).

Example 10

This example illustrates the preparation of the compound of formula II (n=2, R$^1$=p-fluorophenyl) at a multi-kilogram scale. A 30 gallon (120 L) glass-lined reactor was charged with valerolactam (18.0 kg) and toluene (42.0 kg). Trifluoroacetic anhydride (42.0 kg) was added over 30 min and the mixture was stirred for an additional 60 min. Volatiles were distilled off at 60–70° C. at 140 torr. Toluene (50.0 kg) was added and the mixture was further distilled until approximately 27 L remained in the pot and this process was repeated twice. To the residue was added tert-butanol (18.8 kg) and 4-fluorobenzaldehyde (20.3 kg). The resultant solution was slowly transferred to 100 gallon (400 L) glass-lined reactor containing potassium tert-butoxide in tetrahydrofuran (122 kg of a 20% solution). The mixture was warmed to 60° C. for 1 h. Volatiles were distilled at 40–50° C. at 250 torr to a volume of approximately 100 L. Water (180 L) was added to the slurry at 40° C. and the mixture was cooled to 5° C. for 2 h and collected by filtration. The wet cake was washed and reslurried with water (3×200 L) and dried in a tray dryer (50° C., 50 torr) to afford crude 3-p-fluorobenzylidene-2-piperidone (32.6 kg) whose purity by HPLC was 70.3 wt % (95.4 area %).

The crude product was charged to a 100 gallon (400 L) glass-lined reactor with isopropyl acetate (80 kg). Residual water was removed by distillation at atmospheric pressure to a volume of 70 L. Heptane (56 kg) was added at 80° C. and the slurry was cooled to 5° C. Filtration, washing with a mixture of isopropyl acetate (8 kg) and heptane (62 kg) at 5° C., and drying (50° C., 50 torr) afforded purified 3-p-fluorobenzylidene-2-piperidone (20.0 kg, 54%) which by HPLC analysis was 99.1 wt % (99.6 area %).

In order to ensure the material was free from catalyst poisons, a portion of the product (19.7 kg) was further crystallized by dissolution in isopropanol (61.9 kg) and water (20 L) at 75° C. The mixture was seeded at 70° C. and cooled to 30° C. whereupon water (140 mL) was added. After standing overnight, the mixture was cooled to 2° C. and the product was collected by filtration, washed with 10% isopropanol in water (88 L), and dried (65° C., 50 torr). This afforded crystalline 3-p-fluorobenzylidene-2-piperidone (19.5 kg) containing 0.2% residual isopropanol which was 99.7 area % by HPLC. $^{19}$F NMR: δ 112.99; $^1$H NMR: δ 1.88 (m, 2H), 2.80 (m, 2H), 3.45 (m, 2H), 7.08 (m, 3H), 7.40 (m, 2H), 7.77 (s, 1H); $^{13}$C NMR: δ 23.16, 26.37, 42.17, 115.58 (d, 21.4 Hz, C-3'), 129.47(C-3), 131.82 (d, J=8.2 Hz, C-2'), 132.08 (d, J=3.6 Hz, C-1'), 134.65 (olefinic), 162.53 (d, J=249 Hz, C-4'), 166.99 (C-2).

Example 11

This example describes asymmetric hydrogenation at a multi-kilogram scale. A 100 gallon (400 L) glass-lined reactor was charged with recrystallized 3-p-fluorobenzylidene-2-piperidone (19.5 kg), methanol (75 kg, 5 volumes), and dichloromethane (126 kg, 5 volumes). (2S,4S)-(−)-2,4-bis(diphenylphosphino)pentane (97 g, 0.25 mol %) and bis(1,5-cyclooctadiene)iridium(I) tetrafluoroborate (109 g, 0.25 mol %) was added to the stirred solution under nitrogen. The reactor was pressured to 55 psi (0.46 MPa) hydrogen and stirred for 13 h at which time no starting material remained. The solvent was replaced with toluene by successive vacuum distillation and toluene charges and the resultant solution was filtered through a bed of charcoal (Darco G-60) and silica gel 60. The resultant solution contained (S)-3-p-fluorobenzyl-2-piperidone (19.1 kg, 97%); NMR and chiral HPLC analysis as in Example 2 indicated the enantiomeric excess was 91%.

Although particular embodiments of the present invention have been described in the foregoing description, it will be understood by those skilled in the art that the invention is capable of numerous modifications, substitutions, and rearrangements without departing from the spirit or essential attributes of the invention. Reference should be made to the appended claims, rather than to the foregoing specifications, as indicating the scope of the invention.

What is claimed is:

1. A process for the preparation of a compound of formula (I)

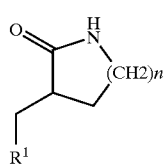

wherein:
$R^1$ is selected from H, $C_{1-6}$ alkyl substituted with 0–3 $R^3$, $C_{3-6}$ cycloalkyl substituted with 0–3 $R^3$, and $C_{6-10}$ aryl substituted with 0–3 $R^3$, and a 5–6 membered heterocycle having 1–2 heteroatoms selected from O, N, and S, the heterocycle being substituted with 0–3 $R^3$;

$R^3$ is selected from $C_{1-4}$ alkyl, $C_{1-4}$ haloalkyl, F, Cl, Br, I, CN, $NO_2$, —S—$R^4$, —O—$R^4$, —$SO_2R^{4a}$, —C(O)$OR^{4a}$, —NHC(O)$R^4$, —C(O)NH$R^4$, —NHC(O)$OR^{4a}$, —OC(O)NH$R^{4a}$, —OC(O)$R^4$, and $C_{6-10}$ aryl substituted with 0–3 $R^5$;

$R^4$ is selected from H, $C_{1-4}$ alkyl, and phenyl;

$R^{4a}$ is selected from $C_{1-4}$ alkyl, and phenyl;

$R^5$ is selected from F, Cl, Br, I, CN, $NO_2$, —S—$R^4$, —O—$R^4$, —$SO_2R^4$, —C(O)$OR^{4a}$, —N($R^4$)$_2$, —NHC(O)$R^4$, —C(O)NH$R^4$, —OC(O)$R^4$, —C(O)$OR^4$, and phenyl;

n is selected from 0, 1, 2, 3;

the process comprising:

contacting a compound of formula (II)

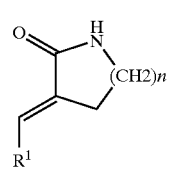

with hydrogen under a suitable pressure in the presence of an iridium complex of the formula ($R^2$)IrL$^+$X$^-$ wherein L is a chelating diene, X is a non coordinating anion, and $R^2$ is selected from

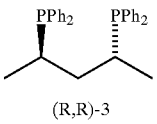 and 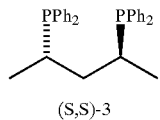

(R,R)-3             (S,S)-3

2. The process of claim 1 wherein the compound of Formula 1 is optically active.

3. The process of claim 2 wherein the compound of Formula 1 has an enantiomeric excess of greater than about 80%.

4. The process of claim 3 wherein the compound of Formula 1 has a high level of enantiomeric purity.

5. The process of claim 4,
wherein
$R^1$ is selected from H, $C_{1-6}$ alkyl substituted with 0–3$R^3$, a $C_{6-10}$ aryl substituted with 0–3 $R^3$, wherein the aryl is selected from phenyl and naphthyl, and a 5–6 membered heterocycle having 1–2 heteroatoms selected from O, N, and S, the heterocycle being substituted with 0–3 $R^3$, the heterocycle being selected from 2-furanyl, 3-furanyl, 2-thienyl, 3-thienyl, oxetanyl, tetrahydrofuranyl, or pyranyl;

$R^3$ is selected from $C_{1-4}$ alkyl, $CF_3$, F, Cl, Br, I, CN, $NO_2$, —O—$R^4$, —C(O)$OR^{4a}$, —NHC(O)$R^4$, —C(O)NH$R^4$, —OC(O)$R^4$, and phenyl substituted with 0–3 $R^5$.

6. The process of claim 5, wherein
$R^1$ is selected from H, $C_{1-6}$ alkyl selected from methyl, ethyl, propyl, i-propyl, butyl, i-butyl, sec-butyl, t-butyl, and pentyl, phenyl substituted with 0–2 $R^3$, furanyl substituted with 0–1 $R^3$; and $R^3$ is selected from $C_{1-4}$ alkyl, $CF_3$, F, Cl, Br, and I.

7. The process of claim 6 wherein
L is selected from 1,5-cyclooctadiene and norbornadiene; and X is selected from $BF_4^-$, $PF_6^-$, $SbF_6^-$, $ClO_4^-$, $AsF_6^-$, $O_3SCF_3^-$, $O_2CCF_3^-$, and $B(C_6F_6)_4^-$.

8. The process of claim 7 wherein the catalyst is generated in the reaction mixture by sequential addition of an iridium complex of Formula $L_2Ir^+X^-$ and 1.0 to 1.1 molar equivalents off (R,R)-3 or (S,S)-3.

9. The process of claim 8 wherein n is selected from 1 and 2.

10. The process of claim 9 wherein $R^1$ is selected from the group consisting of phenyl, p-fluorophenyl, p-methoxyphenyl, p-trifluormethylphenyl, 2-furanyl, or n-propyl.

11. The process of claim 10 wherein the process further comprises filtering the resultant solution through a bed of solid scavenger to remove catalyst residues.

12. The process of claim 11 wherein the process further comprises removal of the reaction solvent by distillation, and crystallizing the product of Formula I to achieve a high level of enantiomeric purity.

* * * * *